United States Patent
Debasish et al.

(10) Patent No.: US 7,519,143 B2
(45) Date of Patent: Apr. 14, 2009

(54) METHOD AND SYSTEM FOR GENERATING A SCATTER CORRECTED X-RAY IMAGE

(75) Inventors: Mishra Debasish, Clifton Park, NY (US); Manoharan Venugopal, Karnataka (IN)

(73) Assignee: General Electric Company, Niskayuna, NY (US)

( * ) Notice: Subject to any disclaimer, the term of this patent is extended or adjusted under 35 U.S.C. 154(b) by 296 days.

(21) Appl. No.: 11/477,756

(22) Filed: Jun. 29, 2006

(65) Prior Publication Data

US 2008/0002807 A1 Jan. 3, 2008

(51) Int. Cl.
 *G01N 23/00* (2006.01)
(52) U.S. Cl. .................... 378/7; 378/4; 378/901
(58) Field of Classification Search ............ 378/4, 378/7, 901; 382/128–131
 See application file for complete search history.

(56) References Cited

U.S. PATENT DOCUMENTS

| | | | | |
|---|---|---|---|---|
| 5,442,672 | A | * | 8/1995 | Bjorkholm et al. ......... 378/4 |
| 5,666,391 | A | * | 9/1997 | Ohnesorge et al. ......... 378/7 |
| 5,909,476 | A | * | 6/1999 | Cheng et al. .............. 378/4 |
| 2006/0008046 | A1 | * | 1/2006 | Ruhrnschopf .............. 378/7 |

OTHER PUBLICATIONS

Baydush et al., Improved image quality in digital mammography with image processing, Jul. 2000, Medical Physics, vol. 27, No. 7, pp. 1503-1508.*

Badea et al., Experiments with nonlinear and chaotic behavior of the multiplicative algebraic reconstruction technique (MART) algorithm for computed tomography, 2004, Physics in Medicine and Biology, vol. 49, pp. 1455-1474.*

Debasish Mishra, Jon P. Longtin, Raman P. Singh, and Vishwanath Prasad; "Performance evaluation of iterative tomography algorithms for incomplete projection data"; Applied Optics / vol. 43, No. 7 / Mar. 1, 2004; p.p. 1522-1532.

D. Mishra et al.; "A Robust Mart Algorithm for Tomographic Applications"; Numerical Heat Transfer, Part B, 35:485-506, 1999.

H. Zaidi, "Reconstruction-Based Estimation of the Scatter Component in Positron Emission Tomography," Ann Nuclear Medlicine Science, vol. 14, No. 3, Sep. 2001, pp. 161-172.

* cited by examiner

*Primary Examiner*—Edward J Glick
*Assistant Examiner*—John M Corbett
(74) *Attorney, Agent, or Firm*—Penny A. Clarke

(57) ABSTRACT

A Digital Radiograph (DR) acquisition system for generating a scatter-corrected X-ray image is provided. The DR acquisition system includes a digital detector configured to produce a two-dimensional (2D) X-ray image of an object of interest. The digital detector is configured to detect X-rays emitted from an X-ray source and transmit the X-rays through the object of interest and generate the 2D X-ray image in response to the detected X-rays. The DR acquisition system further includes an image processor coupled to the digital detector, and a display unit. The image processor is configured to generate projection image data from the 2D X-ray image and iteratively reconstruct the 2D X-ray image to generate a scatter-corrected X-ray image based on the generated projection image data. The display unit configured to display the scatter-corrected X-ray image in conjunction with the 2D X-ray image.

25 Claims, 3 Drawing Sheets

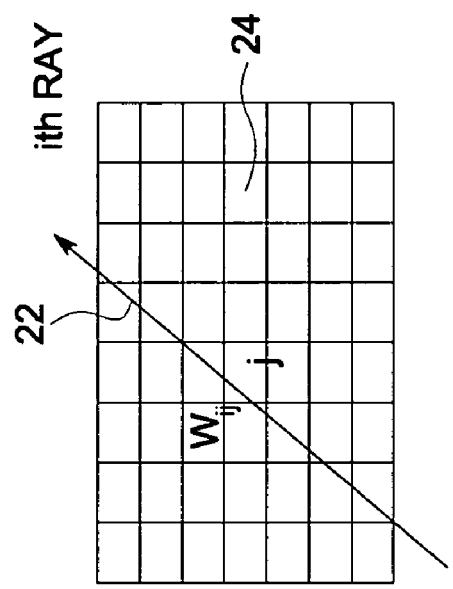
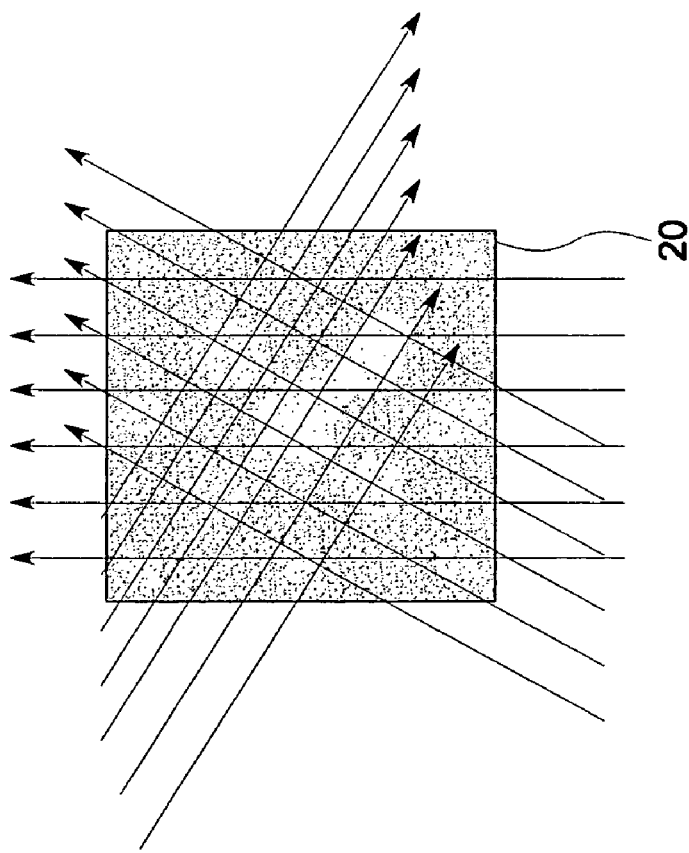
FIG. 2

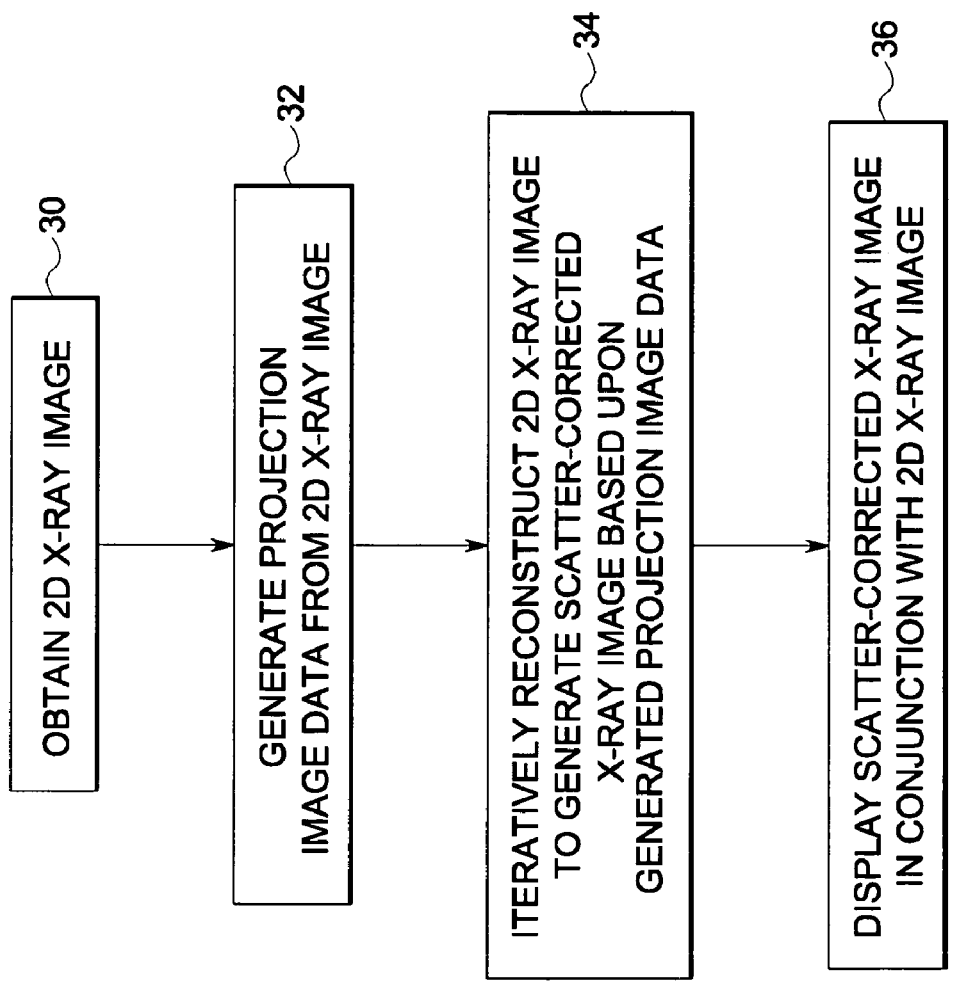

METHOD AND SYSTEM FOR GENERATING A SCATTER CORRECTED X-RAY IMAGE

BACKGROUND

The invention relates generally to digital radiography and more particularly to a system and method for generating a scatter-corrected X-ray image.

The interaction of X-rays with matter is typically affected by material properties and X-ray photon energy. Compton scatter refers to the scattering effect of photons during their interaction with atoms in matter. Compton scatter results in a change in the photon energy level and causes photons to travel in different directions. The low energy scattered photons may further undergo a scattering process or a photoelectric process and the photons that arrive at the detector plane usually have low energy and do not carry any meaningful information. For traditional X-ray imaging processes, these scattered photons represent unwanted photons and are a major cause of image degradation in X-ray imaging techniques. Compton scattering also reduces the contrast of X-ray images. In particular, for applications such as quantitative radiography, where object thickness is related to the intensity of the X-ray images created without the scattered events, large errors may be encountered if the scatter component is not accurately removed.

A number of scatter reduction techniques have been proposed for minimizing the scatter effect in radiographic X-ray images. Some of these techniques include, but are not limited to, Monte-Carlo simulation, Bayesian Image Estimation, Filters, Scatter Kernel Deconvolution, Maximum Likelihood Estimation, Grid techniques, Aperture techniques and Air gap techniques. Monte-Carlo simulation uses artificial random sampling techniques to simulate and study scatter radiation effects. This technique is accurate and simple to simulate. However, it requires a high computational requirement and is time intensive. Bayesian Image Estimation is a post-processing, iterative, non-linear statistical estimation technique that reduces the scatter content while improving the contrast to noise ratio (CNR). This technique is typically used in medical imaging for scatter correction of chest images. However, it is not a generic technique for various types of objects used in industry. Metallic filters or screens may be used to reject low energy photons from the X-ray spectrum. This technique reduces some amount of scatter radiation but does not substantially improve the image quality. Grid techniques have been used successfully in the field of medical X-ray imaging. However, they have not proved to be very useful in industrial applications that have high-energy requirements for industrial inspections. Air-gap techniques reduce the field of view and introduce focal spot blurring. Aperture techniques work with reasonable accuracy but require two different exposures.

While the above techniques separate the scatter contribution from an image to produce a high contrast digital radiograph image with reasonable accuracy, they require intensive computational requirements and/or multiple and long exposures, that increase the radiation dose to a patient and decrease system throughputs. It would therefore be desirable to develop a technique that can efficiently and accurately generate a scatter-free image without the need for intensive computational requirements and multiple or long exposures.

BRIEF DESCRIPTION

In one embodiment, a method of generating a scatter-corrected X-ray image is provided. The method includes obtaining a two-dimensional (2D) X-ray image, generating projection image data from the 2D X-ray image and iteratively reconstructing the 2D X-ray image to generate a scatter-corrected X-ray image based upon the generated projection image data.

In another embodiment, a Digital Radiograph (DR) acquisition system for generating a scatter-corrected X-ray image is provided. The DR acquisition system includes a digital detector configured to produce a two-dimensional (2D) X-ray image of an object of interest. The digital detector is configured to detect X-rays emitted from an X-ray source and transmit the X-rays through the object of interest and generate the 2D X-ray image in response to the detected X-rays. The DR acquisition system further includes an image processor coupled to the digital detector, and a display unit. The image processor is configured to generate projection image data from the 2D X-ray image and iteratively reconstruct the 2D X-ray image to generate a scatter-corrected X-ray image based on the generated projection image data. The display unit is configured to display the scatter-corrected X-ray image in conjunction with the 2D X-ray image.

DRAWINGS

These and other features, aspects, and advantages of the present invention will become better understood when the following detailed description is read with reference to the accompanying drawings in which like characters represent like parts throughout the drawings, wherein:

FIG. 2 is an exemplary illustration of projection image data generated at a plurality of projection view angles in accordance with embodiments of the present invention; and FIG. 3 illustrates a process for generating a scatter-corrected X-ray image in accordance with embodiments of the invention.

DETAILED DESCRIPTION

Figure 1:
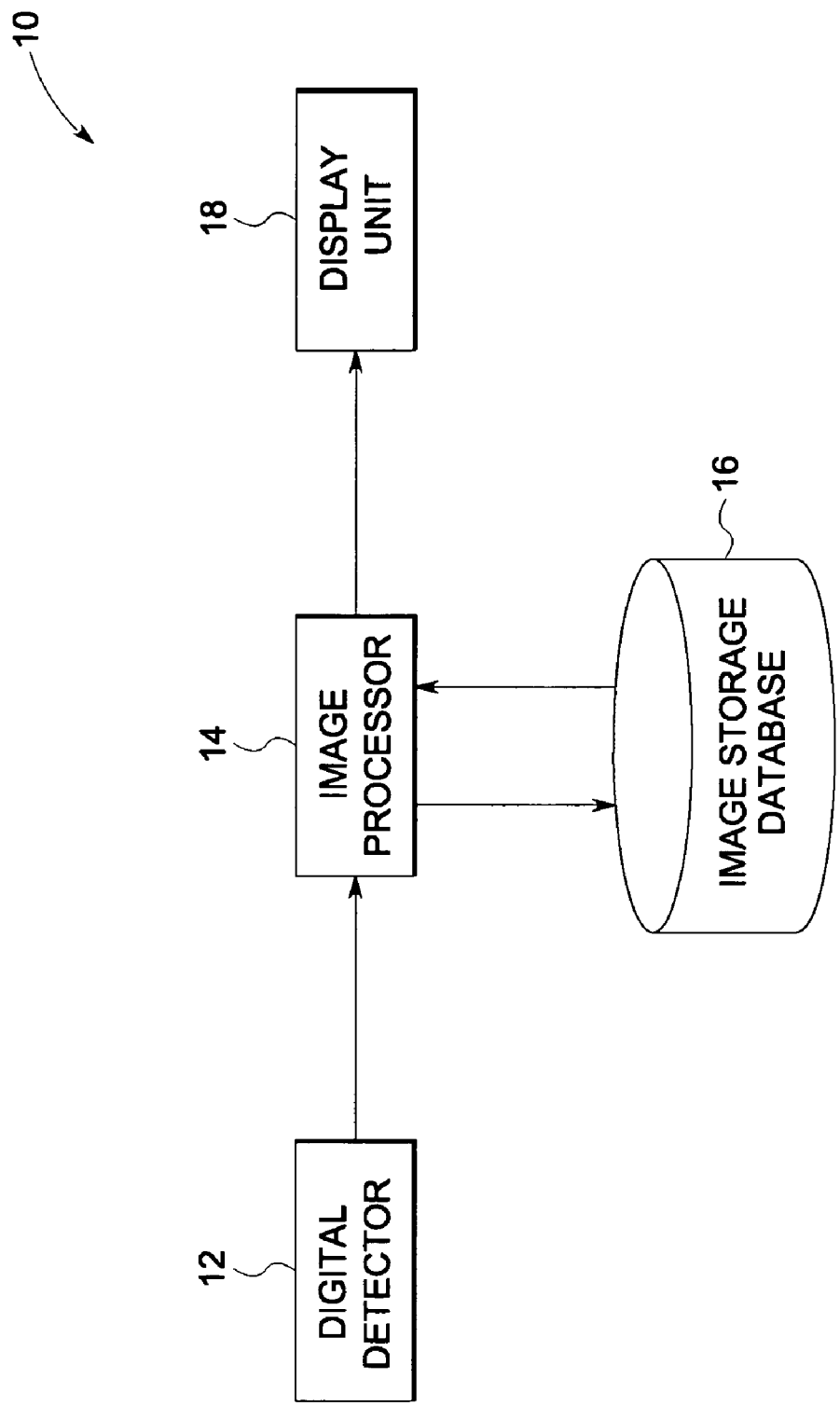
FIG. 1 is an illustration of a digital radiograph (DR) acquisition system for generating a scatter-corrected X-ray image in accordance with embodiments of the invention.

FIG. 1 is an illustration of a Digital Radiograph (DR) acquisition system for generating a scatter-corrected X-ray image in accordance with embodiments of the invention. As shown in FIG. 1, the system 10 includes a digital detector 12, an image processor 14 coupled to the digital detector 12, an image storage database 16 and a display unit 18. Exemplary digital detectors 12 include digital X-ray detectors, non-limiting examples of which include two-dimensional (2D) amorphous silicon (a-Si) array detectors. The digital detector 12 detects X-rays emitted from a radiation source (not shown in FIG. 1) and transmitted through an object of interest to generate a two-dimensional (2D) X-ray image. Exemplary radiation sources include X-ray sources and gamma ray sources. Although the illustrated examples depict X-rays as an exemplary type of radiation for radiographic imaging, it will be appreciated that the disclosed invention is also applicable to other radiation types, such as gamma rays.

As used herein, the phrase "generating an image" is not intended to exclude embodiments of the present invention in which data representing an image is generated but a viewable image is not. However, many embodiments generate (or are configured to generate) at least one viewable image. Similarly, the phrase "processing an x-ray image" is not intended to exclude embodiments of the present invention in which data representing an X-ray image is processed.

In accordance with embodiments of the present invention, the image processor 14 is configured to process the 2D X-ray image. It should be noted that the present invention is not limited to any particular processor for performing the processing tasks of the invention. The term "processor," as used herein, is intended to denote any machine capable of performing the calculations, or computations, necessary to perform the tasks of the invention. The term "processor" is intended to denote any machine that is capable of accepting a structured input and of processing the input in accordance with prescribed rules to produce an output. It should also be noted that the phrase "configured to" as used herein means that the processor is equipped with a combination of hardware and software for performing the tasks of the invention, as will be understood by those skilled in the art. In a particular embodiment, and as will be described in greater detail below, the image processor 14 processes the 2D X-ray image to generate projection data at a plurality of projection view angles and iteratively reconstructs the 2D X-ray image to generate a scatter-corrected X-ray image, based upon the generated projection data. As used herein, "projection data" refers to a plurality of line integrals of attenuation coefficients of an imaged object, computed along certain prescribed directions. In one embodiment, the line integrals are generated using parallel beam geometry. However, the line integrals may also be generated using fan-beam geometry. FIG. 2 illustrates exemplary projection data, as discussed in greater detail below.

In a particular embodiment, the image processor 14 is configured to iteratively reconstruct the 2D X-ray image to generate an X-ray image due to scatter based upon a scatter component in the 2D X-ray image. As used herein, the "scatter component" refers to projection image data lying in a low frequency domain in the 2D X-ray image. As used herein, the "low frequency domain" refers to a domain that does not substantially vary spatially over an image region. As will be appreciated by those skilled in the art, the scatter contribution in an X-ray image generally lies in low spatial frequency regions of the image and the scatter component in an X-ray image generally refers to the low spatial frequency component in the generated projection image data. In accordance with one embodiment, an iterative reconstruction technique is used to separate a majority of the low spatial frequencies, which are dominant in the image to enable the convergence of the lower spatial frequencies at an earlier reconstruction stage and the convergence of the higher spatial frequencies at a later stage. The spatial frequency convergence may be controlled by suitably selecting the angles of projections and the relaxation factor to be used during the reconstruction. In an exemplary embodiment, orthogonal sets of projections (that is, projections that are 90 degrees apart) are not included to prevent higher spatial frequency content such as sharp edges in the reconstructed image.

In accordance with embodiments of the present invention, the line-integral projection data is generated at a plurality of view angle projections, using the recorded 2D X-ray image as input. The projection data is used to iteratively reconstruct the 2D X-ray image to generate the scatter-corrected X-ray image. In a particular embodiment, the image processor 14 uses an average multiplicative algebraic reconstruction (MART) technique to iteratively reconstruct the 2D X-ray image. The image processor 14 is then configured to separate the X-ray image due to scatter from the 2D X-ray image to recover the scatter-corrected X-ray image. In a particular embodiment, the X-ray image due to scatter is "subtracted" from the 2D X-ray image to recover the scatter-corrected X-ray image.

As will be appreciated by those skilled in the art, algebraic reconstruction techniques (ART) refer to series based expansion techniques used in tomographic algorithms. ART techniques, are, in general, based on discretizing a given volume to be reconstructed into several two-dimensional planes, wherein each plane is further discretized into a rectangular grid of cells. The X-ray radiation that passes through and interrogates this measurement volume is represented by a collection of rays.

FIG. 2 is an exemplary illustration of projection image data generated at a plurality of projection view angles in accordance with embodiments of the present invention. As illustrated in FIG. 2, reference numeral 20 illustrates a collection of projection image data or rays generated at a plurality of projection view angles. Reference numeral 22 illustrates a given ray "i", passing through a series of cells 24, where the path of the ray, i, is determined by the geometry of the test medium, the optical system and the radiation source. As will be appreciated by those skilled in the art, the total influence of the medium on the ray i, is the summation of each cell's contribution. The projection data may be approximated by the summation shown in equation (1) below:

$$\phi_i = \sum_{j=1}^{N} w_{ij} f_j \qquad (1)$$

$$i = 1, 2, \ldots, M, N > M.$$

where, $\Phi i$ is the total influence on the ray i by the medium, N is the number of cells that the $i^{th}$ ray traverses, M is the number of rays, $w_{ij}$ is the weight function computed on a local grid and $f_j$ is the field value (for example, the temperature or density) in the $j^{th}$ cell. In particular, the weight function $w_{ij}$ represents the contribution of cell j to the measured projection from ray, i. As may be observed from FIG. 2, the weight function, $w_{ij}$ is the length of the intercept of the $i^{th}$ ray with the $j^{th}$ cell for a given projection view angle.

Equation (1) may also be expressed as a matrix equation as shown in equation (2) below:

$$[w_{ij}]\{f_j\} = \{\phi_i\} \qquad (2)$$

Since the weight function $w_{ij}$ is known and the projection data $\Phi$ may be obtained from experimental measurements, the iterative reconstruction technique calculates a generalized inverse of $[w_{ij}]$ by inverting the rectangular matrix $[w_{ij}]$ to find $\{f_j\}$.

As will be appreciated by those skilled in the art, iterative reconstruction techniques are based on computing a simulated projection for a given projection view angle by computing an estimate of one or more variables in each iteration. The result is compared with the actual data for the same angle, and an error term is computed based on the difference between the simulated values and the actual values. From this error, corrections are made to the field variable. The process is repeated for another projection angle, and corrections are again calculated. Once all the projection angles are complete and the corrections are implemented from all the measured projection angles, the field values are compared with those from the previous iteration. If the difference is less than some prescribed value, a converging solution is said to be achieved.

Iterative algorithms may be divided into two categories based on the particular technique used to update corrections for the field variables. Iterative algorithms with additive corrections are known as algebraic reconstruction techniques (ART) whereas those based on multiplicative corrections are known as multiplicative reconstruction techniques (MART).

Many variations of the ART algorithm are known in the art, such as $ART_1$, $ART_2$ and $ART_3$, and these techniques are in general based on determining an initial guess of the field to be reconstructed, calculation of the correction of the guessed field, application of the correction, and testing for convergence or the stopping criterion, as will be described in greater detail below.

In the $ART_1$ algorithm, corrections are applied through a weight factor computed as an average correction along a ray. If $\Phi_{i\theta}$ is the projection data from the $i^{th}$ ray in the $\theta$ projection direction of the projection and fi is the initial guess of the field value, the estimated projection $\tilde{\Phi}_{i\theta}$ using the current field value is defined by equation (3) below:

$$\tilde{\phi}_{i\theta} = \sum_{j=1}^{N} w_{i\theta,j} f_j \quad (3)$$

$$i\theta = 1, 2, \ldots, M_\theta$$

Equation (4) represents the correction for the projection data. The correction is calculated as the ratio between the recorded projection data $\Phi_{i\theta}$ and the calculated projection data from the guessed field, $\tilde{\Phi}_{i\theta}$, that is being iterated. The total value of the weight function along the $i^{th}$ ray is determined by equation (5) as shown below:

$$\Delta\phi_{i\theta} = \frac{\phi_{i\theta}}{\tilde{\phi}_{i\theta}} \quad (4)$$

$$W_{i1} = \sum_{j=1}^{N} w_{i\theta,j} \quad (5)$$

The average value of the correction along the $i^{th}$ ray is shown in equation (6) and $$\Delta\overline{\phi_{i\theta}} = \frac{\Delta\phi_{i\theta}}{W_{i\theta}}, \quad (6)$$

the field values are updated as shown in equation (7)

$$f_j^{new} = f_j^{old} + \mu\Delta\overline{\phi_{i\theta}}, \quad (7)$$

where $\mu$ is the relaxation factor. The calculated projections are then computed once for a particular angle and remain unchanged until the iteration through all rays for a given angle is complete, even though the field values are continuously updated.

In the $ART_2$ algorithm, corrections are applied to all the cells through which the $i^{th}$ ray passes by use of the weight factor $w_{i\theta,j}$. The generated projections are updated after the calculation through each ray using equations (8) and (9) as shown below:

$$W_{i\theta} = \sum_{j=1}^{N} (w_{i\theta,j})^2, \quad (8)$$

$$f_j^{new} = f_j^{old} + \mu\frac{\Delta\phi_{i\theta} w_{i\theta,j}}{W_{i\theta}}. \quad (9)$$

The $ART_3$ algorithm is also referred to as the simultaneous iterative reconstruction technique. In this algorithm, variables are updated after all correction values for the individual cells have been calculated. The numerically generated projections are computed once for all angles and are updated only after the calculations have been completed for all rays. At each iteration, every cell is examined for those rays that pass through it. The rays passing through a given cell contribute to a correction that is determined by the weight factor $w_{i\theta,j}$. An average of these corrections is then introduced into the field variable for the cell. If $c_j$ is the total number of rays passing through a given cell j, the corrections may be implemented using equation (10) below:

$$f_j^{new} = f_j^{old} + \frac{1}{c_j}\sum_{c_j} \mu\frac{w_{i\theta,j}\Delta\phi_{i\theta}}{W_{i\theta}}, \quad (10)$$

where $W_{i\theta}$ may be computed using equation (8)

As mentioned above, when the corrections in an iterative reconstruction algorithm are multiplicative in nature rather than additive, the algorithms may be grouped under the MART family of algorithms. The method of implementing corrections for the MART family of algorithms is similar to $ART_2$. However, instead of computing the difference, $\Phi_{i\theta} - \tilde{\Phi}_{i\theta}$, as in ART algorithms, the ratio may be computed as follows:

$$\Delta\phi_{i\theta} = \frac{\phi_{i\theta}}{\phi'_{i\theta}}. \quad (11)$$

As will be appreciated by those skilled in the art, several variations of the MART algorithm exist such as, $MART_1$, $MART_2$ and $MART_3$. These algorithms are distinguished from the way corrections are implemented and may be represented generally, by equation (12) as shown below:

$$MART_1: f_j^{new} = f_j^{old}(1 - \mu\Delta\phi_{i\theta}), \quad (12)$$

$$MART_2: f_j^{new} = f_j^{old}\left[1 - \mu\frac{w_{i\theta,j}}{(w_{i\theta,j})_{max}}(1 - \Delta\phi_{i\theta})\right],$$

$$MART_3: f_j^{new} = f_j^{old}(\Delta\phi_{i\theta})^{\frac{\mu w_{i\theta,j}}{(w_{i\theta,j})_{max}}}.$$

As may be observed from equation (12), in $MART_1$, the weight function is prescribed in binary form, being unity if a particular ray passes through a pixel and zero otherwise. In $MART_2$ and $MART_3$, the weight function is calculated as the ratio of the length of the ray intercepted by the pixel and the maximum dimension of a segment enclosed by it.

In accordance with embodiments of the present invention, the image processor 14 uses an average multiplicative algebraic reconstruction (AVMART) technique to iteratively reconstruct the 2D X-ray image to generate a scatter-corrected X-ray image. The AVMART algorithms are similar in implementation with the MART algorithms, but the corrections are applied considering all rays from all angles passing through a given cell. Therefore, instead of a single correction obtained from individual rays, an "average correction" estimated from all rays for a given cell is used. The correction of each pixel is updated on the basis of the $N^{th}$ root of the product of all the corrections from all the N rays of all view angles passing through a pixel. The technique of average corrections used by the AVMART algorithms perform better in the presence of noisy projection data and are desensitized to noise. Three variations of the AVMART algorithm exist, and are shown in equations (13), (14) and (15) below:

$$AVMART_1: f_j^{new} = f_j^{old} \left[ \prod_{c_j} (1 - \mu \Delta \phi_{i\theta}) \right]^{\frac{1}{c_j}}, \quad (13)$$

$$AVMART_2: f_j^{new} = f_j^{old} \left\{ \prod_{c_j} \left[ 1 - \mu \frac{w_{i\theta,j}}{(w_{i\theta,j})_{max}} \times (1 - \Delta \phi_{i\theta}) \right] \right\}^{\frac{1}{c_j}}, \quad (14)$$

$$AVMART_3: f_j^{new} = f_j^{old} \left[ \prod_{c_j} (\Delta \phi_{i\theta})^{\frac{\mu w_{i\theta,j}}{(w_{i\theta,j})_{max}}} \right]^{\frac{1}{c_j}}. \quad (15)$$

Referring to FIG. 1 again, in certain embodiments, the image processor 14 is configured to iteratively reconstruct the 2D X-ray image using a relaxation factor. The "relaxation factor" determines the percentage of error to be distributed during each iteration of reconstruction. As will be appreciated by those skilled in the art, the particular choice of values assigned to the relaxation factor affects the image quality and the convergence criteria in an iterative reconstruction procedure. In a particular embodiment, the image processor 14 is configured to derive a plurality of optimal values for the relaxation factor, to generate the scatter-corrected X-ray image.

As will be appreciated by those skilled in the art, over-relaxing the X-ray acquisition system assists in the early the convergence of the scatter field. However, the image is generally scaled back using a scaling factor. In an exemplary implementation, the relaxation factor is a close estimate of the scaling factor. In one embodiment, the values of the relaxation factor are in the range of 1.2-1.6. In a particular embodiment, experiments using narrow beam collimated geometry are performed to identify the required relaxation parameter for a particular material and at a particular X-ray energy level. The reconstructed images are then scaled down by the relaxation factor.

The image processor 14 is then configured to separate the X-ray image due to scatter from the 2D X-ray image to recover the scatter-corrected X-ray image. In an exemplary implementation of the present invention, the X-ray image due to scatter is "subtracted" from the 2D X-ray image to recover the scatter-corrected X-ray image. The scatter-corrected X-ray image may then displayed in conjunction with the 2D X-ray image. In certain embodiments, the image processor 14 may perform a validation of the scatter-corrected X-ray image. In one embodiment, the validation of the scatter-corrected X-ray image is performed using an aperture technique. Two exposures of the imaged object at the same X-ray energy level are generated, one with a lead sheet containing a few drilled small apertures (approximately 1 mm-2 mm in diameter) and placed in front of the object, and one without a lead sheet. As will be appreciated by those skilled in the art, the use of a lead sheet blocks the radiation due to scatter and allows the primary radiation to pass through the drilled apertures. The X-ray signal measured in a small region of interest in the projected image spot of the aperture in the lead sheet accordingly represents a good estimate of a scatter free signal. The measured signal is then compared with the scatter corrected signal to perform a validation of the scatter-corrected X-ray image.

In another embodiment, a Susan filter or an anisotropic diffusion filter may further be applied to the scatter-corrected X-ray image to generate a noise reduced scatter-corrected X-ray image. As used herein, an "improved scatter-corrected X-ray image" refers to an image with an improved contrast to noise ratio (CNR).

In an alternate embodiment, the image processor 14 is configured to generate a "reduced" 2D X-ray image wherein the steps of generating the projection image data and iteratively reconstructing the 2D X-ray image may be performed on the reduced 2D X-ray image. In one embodiment, the reduced image is generated using at least one of a decimation technique or an interpolation technique. The generation of a reduced X-ray image reduces the computational cost associated with the processing of digital radiograph images, which are generally large in size (typically in the range of 2304× 1920 pixels or 1024×1024 pixels).

Referring to FIG. 1 again, the image storage database 16 stores the digital radiograph images as digital data. The display unit 18 displays the scatter-corrected X-ray image in conjunction with the 2D X-ray image.

FIG. 3 illustrates a process for generating a scatter-corrected X-ray image in accordance with embodiments of the invention. In step 30, a two-dimensional (2D) X-ray image is obtained. In step 32, projection image data is generated from the 2D X-ray image. As mentioned above, the projection image data is generated at a plurality of projection view angles. In step 34, the 2D X-ray image is iteratively reconstructed to generate a scatter-corrected X-ray image based upon the generated projection image data. In one embodiment and as mentioned above, iteratively reconstructing the 2D X-ray image includes generating an X-ray image due to scatter, based upon a scatter component in the 2D X-ray image. The "scatter component" includes projection image data lying in a low frequency domain in the 2D X-ray image. In a particular embodiment, and as mentioned above, the iterative reconstruction is performed using an AVMART technique. In a more particular embodiment, the AVMART technique uses a relaxation factor and derives a plurality of optimal values for the relaxation factor to generate the scatter-corrected X-ray image.

The X-ray image due to scatter is then separated from the 2D X-ray image to recover the scatter-corrected X-ray image. In an exemplary implementation of the present invention, the X-ray image due to scatter is subtracted from the 2D X-ray image to recover the scatter-corrected X-ray image. In step 36, the scatter-corrected X-ray image is displayed in conjunction with the 2D X-ray image. In certain embodiments, a validation of the generated scatter-corrected X-ray image may further be performed.

In another embodiment, a Susan filter or an anisotropic diffusion filter may further be applied to the scatter-corrected X-ray image to generate an improved scatter-corrected X-ray image.

In certain embodiments, and as mentioned above, a reduced X-ray image may be generated and the steps of generating the projection image data and iteratively reconstructing the 2D X-ray image may be performed on the reduced X-ray image. Further, the reduced X-ray image may be generated using at least one of a decimation technique or an interpolation technique.

In addition, the scatter-corrected X-ray image generated in accordance with embodiments of the present invention may be used to perform quantitative radiography. As known to those skilled in the art, quantitative radiography involves estimating the length of the material through which an X-ray photon has traveled. The present invention facilitates quantitative radiography since scatter corrected images can be used easily with a standard calibration data set to estimate the thickness of materials using X-ray images.

Embodiments of the present invention disclose a technique for improving the image quality of recorded digital 2D X-ray images by creating line integral projection data from the X-ray image and using this information to separate the scatter contribution from the X-ray image. The disclosed technique may be implemented directly with the X-ray image without requiring any extra modifications during data acquisitions, radiation dose and exposure time. A scatter-corrected X-ray image is generated by iteratively reconstructing the recorded 2D X-ray image based upon the generated projection line integral information.

The disclosed embodiments have several advantages including the use of the AVMART technique to separate spatial frequency convergence during iterations, the use of Susan or Anisotropic diffusion filters to improve the CNR of the scatter corrected X-ray image and the optimization of the relaxation factor during iterative reconstruction. Further, the disclosed embodiments may be applied to both industrial and medical images.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of generating a scatter-corrected X-ray image, the method comprising:
   obtaining a two-dimensional (2D) X-ray image;
   generating projection image data from the 2D X-ray image; and
   iteratively reconstructing the 2D X-ray image to generate a scatter-corrected X-ray image based upon the generated projection image data, wherein iteratively reconstructing the 2D X-ray image comprises using a multiplicative algebraic reconstruction (MART) technique.

2. The method of claim 1, wherein generating projection image data comprises
   generating simulated projection image data from the 2D X-ray image, and wherein
   iteratively reconstructing the 2D X-ray image to generate a scatter-corrected X-ray image is performed based upon the simulated projection image data.

3. The method of claim 2, wherein the simulated projection image data is generated at a plurality of projection view angles using the 2D X-ray image as input, and wherein the simulated projection image data represents a plurality of line integrals of attenuation coefficients of a scanned object corresponding to the 2D X-ray image.

4. The method of claim 1, wherein the multiplicative algebraic reconstruction (MART) technique is an average multiplicative algebraic reconstruction (AVMART) technique.

5. The method of claim 1, wherein iteratively reconstructing the 2D X-ray image comprises generating an X-ray image due to scatter, based upon a scatter component of the 2D X-ray image.

6. The method of claim 5, wherein the scatter component comprises projection image data lying in a low spatial frequency domain in the 2D X-ray image.

7. The method of claim 5, further comprising separating the X-ray image due to scatter from the 2D X-ray image to recover the scatter-corrected X-ray image.

8. The method of claim 1, further comprising generating a reduced X-ray image, wherein the steps of generating the projection image data and iteratively reconstructing the 2D X-ray image are performed on the reduced 2D X-ray image.

9. The method of claim 8, wherein generating the reduced 2D X-ray image comprises using at least one of a decimation technique or an interpolation technique.

10. The method of claim 1, further comprising displaying the scatter-corrected X-ray image in conjunction with the 2D X-ray image.

11. The method of claim 1, further comprising performing a validation of the generated scatter-corrected X-ray image.

12. The method of claim 1, wherein the scatter-corrected X-ray image is used to perform quantitative radiography.

13. A method of generating a scatter-corrected X-ray image, the method comprising:
   obtaining a two-dimensional (2D) X-ray image;
   generating projection image data from the 2D X-ray image; and
   iteratively reconstructing the 2D X-ray image to generate a scatter-corrected X-ray image based upon the generated projection image data, wherein iteratively reconstructing the 2D X-ray image comprises:
   generating an X-ray image due to scatter, based upon a scatter component of the 2D X-ray image, and
   using a relaxation factor and deriving a plurality of optimal values for the relaxation factor, to generate the scatter-corrected X-ray image.

14. A method of generating a scatter-corrected X-ray image, the method comprising:
   obtaining a two-dimensional (2D) X-ray image;
   generating projection image data from the 2D X-ray image;
   iteratively reconstructing the 2D X-ray image to generate a scatter-corrected X-ray image based upon the generated projection image data; and
   applying at least one of a Susan filter or an anisotropic diffusion filter to the scatter-corrected X-ray image to generate a noise-reduced scatter-corrected X-ray image.

15. A Digital Radiograph (DR) acquisition system for generating a scatter-corrected X-ray image, the DR acquisition system comprising:
   a digital detector configured to produce a two-dimensional (2D) X-ray image of an object of interest, wherein the digital detector is configured to:
   detect a plurality of X-rays emitted from an X-ray source and transmitted through the object of interest; and
   generate the 2D X-ray image in response to the detected X-rays;
   an image processor coupled to the digital detector configured to process the 2D X-ray image, wherein the image processor is configured to:
   simulate projection image data from the 2D X-ray image; and
   iteratively reconstruct the 2D X-ray image to generate a scatter-corrected X-ray image by applying an iterative algorithm that compares the simulated projection image data with a plurality of actual data for the 2D X-ray image to achieve a converging solution, wherein the image processor uses a multiplicative algebraic reconstruction (MART) technique to iteratively reconstruct the 2D X-ray image.

16. The digital radiograph (DR) acquisition system of claim 15, wherein the image processor is further configured to simulate the projection image data at a plurality of projection view angles, and wherein the projection image data represents a plurality of line integrals of attenuation coefficients of the object.

17. The digital radiograph (DR) acquisition system of claim 15, wherein the multiplicative algebraic reconstruction (MART) technique is an average multiplicative algebraic reconstruction (AVMART) technique.

18. The digital radiograph (DR) acquisition system of claim 15, wherein the image processor is further configured to generate an X-ray image due to scatter based upon a scatter component of the 2D X-ray image.

19. The digital radiograph (DR) acquisition system of claim 18, wherein the scatter component comprises projection image data lying in a low spatial frequency domain in the 2D X-ray image.

20. The digital radiograph (DR) acquisition system of claim 15, wherein the image processor is further configured to separate the X-ray image due to scatter from the 2D X-ray image to recover the scatter-corrected X-ray image.

21. The digital radiograph (DR) acquisition system of claim 15, wherein the image processor is configured to generate a reduced X-ray image, wherein the steps of generating the projection image data and iteratively reconstructing the 2D X-ray image are performed on the reduced 2D X-ray image.

22. The digital radiograph (DR) acquisition system of claim 21, wherein the image processor is further configured to apply at least one of a decimation technique or an interpolation technique to generate the reduced X-ray image.

23. The digital radiograph (DR) acquisition system of claim 15, wherein the image processor is further configured to validate the generated scatter-corrected X-ray image.

24. The digital radiograph (DR) acquisition system of claim 15 further comprising a display unit configured to display the scatter-corrected X-ray image in conjunction with the 2D X-ray image.

25. A digital radiograph (DR) acquisition system for generating a scatter-corrected X-ray image, the DR acquisition system comprising:
    a digital detector configured to produce a two-dimensional (2D) X-ray image of an object of interest, wherein the digital detector is configured to:
        detect a plurality of X-rays emitted from an X-ray source and transmitted though the object of interest; and
        generate the 2D X-ray image in response to the detected X-rays;
    an image processor coupled to the digital detector configured to process the 2D X-ray image, wherein the image processor is configured to:
        generate projection image data from the 2D X-ray image,
        iteratively reconstruct the 2D X-ray image to generate a scatter-corrected X-ray image based on the generated projection image data, and
        iteratively reconstruct the 2D X-ray image using a relaxation factor, and wherein the image processor is configured to derive a plurality of optimal values for the relaxation factor, to generate the scatter-corrected X-ray image.

* * * * *

UNITED STATES PATENT AND TRADEMARK OFFICE
CERTIFICATE OF CORRECTION

PATENT NO. : 7,519,143 B2
APPLICATION NO. : 11/477756
DATED : April 14, 2009
INVENTOR(S) : Debasish et al.

It is certified that error appears in the above-identified patent and that said Letters Patent is hereby corrected as shown below:

On the Title Page, in Field (56), under "OTHER PUBLICATIONS", in Column 2, Line 12, delete "Medlicine" and insert -- Medicine --, therefor.

In Column 4, Line 29, delete "Φi" and insert -- $\Phi_i$ --, therefor.

In Column 5, Line 12, delete " $\Phi_{i\theta} \text{using}$ " and insert -- $\tilde{\Phi}_{i\theta} \text{using}$ --, therefor.

In Column 5, Line 25, delete " $\Phi_{i\theta}$, " and insert -- $\tilde{\Phi}_{i\theta}$, --, therefor.

In Column 5, Line 30, in Equation (4), delete " $\Delta\phi_{i\theta} = \dfrac{\phi_{i\theta}}{\phi_{i\theta}}$ " and insert -- $\Delta\phi_{i\theta} = \dfrac{\phi_{i\theta}}{\tilde{\phi}_{i\theta}}$ --, therefor.

In Column 12, Line 15, in Claim 25, delete "though" and insert -- through --, therefor.

Signed and Sealed this

Twenty-ninth Day of September, 2009

David J. Kappos
*Director of the United States Patent and Trademark Office*